(12) United States Patent
Briffa et al.

(10) Patent No.: US 7,800,364 B2
(45) Date of Patent: Sep. 21, 2010

(54) DEVICE FOR INSPECTING TANGENTIAL RECESSES IN A ROTOR DISK

(75) Inventors: Patrick Briffa, Nay (FR); Patrick Cabanis, Ozouer le Voulgis (FR); Rene Le Floc'h, Moret sur Loing (FR); Christian Armand Marceau, Lieusaint (FR); Dominique Thibault, Nandy (FR); Vincent Pasquer, Forges les Bains (FR)

(73) Assignees: SNECMA, Paris (FR); SNECMA Services, Paris (FR)

( * ) Notice: Subject to any disclaimer, the term of this patent is extended or adjusted under 35 U.S.C. 154(b) by 0 days.

(21) Appl. No.: 12/436,829

(22) Filed: May 7, 2009

(65) Prior Publication Data

US 2009/0267598 A1    Oct. 29, 2009

Related U.S. Application Data

(63) Continuation of application No. 12/211,357, filed on Sep. 16, 2008, now abandoned.

(30) Foreign Application Priority Data

Sep. 19, 2007    (FR) .................................. 07 57669

(51) Int. Cl.
*G01N 27/82* (2006.01)

(52) U.S. Cl. ...................................... 324/240; 324/228

(58) Field of Classification Search ................. 324/240, 324/228
See application file for complete search history.

(56) References Cited

U.S. PATENT DOCUMENTS

| 4,970,890 | A | 11/1990 | Jaafar et al. |
|---|---|---|---|
| 5,442,286 | A | 8/1995 | Sutton, Jr. et al. |
| 6,608,478 | B1 | 8/2003 | Dziech et al. |
| 6,952,094 | B1 | 10/2005 | Viertl |
| 7,107,695 | B2 | 9/2006 | Paillarse et al. |
| 7,305,898 | B2 | 12/2007 | Cabanis et al. |
| 2008/0265878 | A1 | 10/2008 | Bousquet et al. |
| 2008/0265879 | A1 | 10/2008 | Briffa et al. |
| 2008/0297148 | A1 | 12/2008 | Cabanis et al. |

FOREIGN PATENT DOCUMENTS

EP    1 416 122 A2    5/2004

*Primary Examiner*—Reene Aurora
(74) *Attorney, Agent, or Firm*—Oblon, Spivak, McClelland, Maier & Neustadt, L.L.P.

(57) ABSTRACT

An inspection device for inspecting tangential recesses in a rotor disk by means of eddy currents is disclosed. The device includes a probe containing a plurality of sensors arranged to acquire a plurality of data series during a scan stroke, and the probe is mounted on moving equipment that is slidable in a support that is provided with two positioning members for co-operating with recesses neighboring the recess for inspection.

6 Claims, 2 Drawing Sheets

DEVICE FOR INSPECTING TANGENTIAL RECESSES IN A ROTOR DISK

CROSS-REFERENCE TO RELATED APPLICATIONS

The present application is a continuation of U.S. application Ser. No. 12/211,357 filed Sep. 16, 2008, which claims priority to FR 07 57669.

The invention relates to a device for inspecting tangential recesses or slots in a turbomachine rotor disk by using eddy currents. More particularly, the invention relates to an improvement making it possible in particular to position inspection means quickly and accurately, to acquire data rapidly, and to make measurements that are more reliable and more accurate. More particularly, the device is adapted to inspect the pressure surfaces of said tangential recesses.

BACKGROUND OF THE INVENTION

A so-called "multi-element" eddy current probe is known that is associated with an imaging system, the probe being specially shaped to slide along a tangential recess in a rotor disk. The rectilinear probe is of constant section; its cross-section has an outline that corresponds to the section of the recess for inspection. It contains a plurality of eddy current sensors arranged for quasi-simultaneous acquisition of a plurality of data series during a scanning stroke in the longitudinal direction of the recess. Each data series corresponds to scanning a longitudinal strip of the inside surface of the recess by means of a single sensor. The probe is moved manually.

The reliability and the accuracy of the measurement depend on the probe being properly positioned in the recess. That is why the sensors are grouped together in a central segment of the probe, between two guide segments that do not have sensors. This ensures that the probe is properly positioned, even at the ends of the recess when the sensors begin to scan the surface state of the recess.

Although associating such a multi-element probe with an imaging system is advantageous, the performance of the system is limited by the presence of the guide segments, i.e. by the impossibility of placing the sensors at the end of the probe. As a result, inspection is not genuinely reliable, unless the central segment of the probe is caused to slide over the entire length of the recess. That can be done on a disk that has been completely dismantled so that the probe can be inserted via one end of the recess and extracted from the other. However, if it is necessary to inspect a rotor made up of a plurality of disks positioned side by side (welded together), then such movement is not always possible.

OBJECT AND SUMMARY OF THE INVENTION

The invention makes it possible to improve the conditions under which such a multi-element probe can be used for inspecting tangential recesses in a rotor disk, in particular for inspecting the pressure faces of the recesses.

More precisely, the invention provides an inspection device for inspecting tangential recesses in a rotor disk by means of eddy currents, the device being of the type comprising a probe of cross-section with an outline that matches the outline of the section of such a recess, said probe containing a plurality of sensors arranged for acquiring a plurality of data series during a scan stroke in the longitudinal direction of the recess, comprising both a support having two positioning members that co-operate respectively with two recesses neighboring the recess for inspection, and sliding moving equipment carrying said probe and arranged to guide it along said recess during inspection.

With the above-defined arrangement, the positioning of the probe is accurate from the beginning of its stroke inside the recess and the measurements are therefore more reliable and more accurate. Progress of the probe along the recess can be controlled more easily, even by hand. In addition, according to another characteristic that is advantageous, the sensors may be distributed over a long length of the probe, or even over substantially its entire length, including in the vicinity of its ends. In other words, the above-mentioned guide segments can be omitted, thereby making it possible to scan recesses better over their entire lengths, even when the disk is beside another disk.

According to another advantageous characteristic, the probe is made up of two moving blocks. The sensors are distributed within the blocks. The blocks are hinge-mounted and they are biased resiliently outwards (away from each other) so as to guarantee that said blocks make contact with the corresponding zones of the recess for inspection. In particular, these zones include the above-mentioned pressure surfaces.

Furthermore, indexing means may be provided to monitor the position and/or the advance of the probe within the recess for inspection.

In one possible embodiment, both positioning members include expandable elements that are spaced apart from each other by a distance corresponding to the distance between said neighboring recesses. These elements are shaped and arranged so as to be engaged and locked in said neighboring recesses, thereby enabling the support to be positioned in such a manner that said probe can be engaged in said recess for inspection.

Advantageously, the device includes a multi-channel generator-receiver. Such a generator-receiver serves to activate all of the sensors simultaneously at different positions along the probe within said recess for inspection. During a reception stage, it serves to synchronize acquisitions.

The invention can be better understood and other advantages thereof appear more clearly in the light of the following description of an inspection device using eddy currents in accordance with the principle of the invention, given purely by way of example and made with reference to the accompanying drawings, in which:

MORE DETAILED DESCRIPTION

Figure 1:
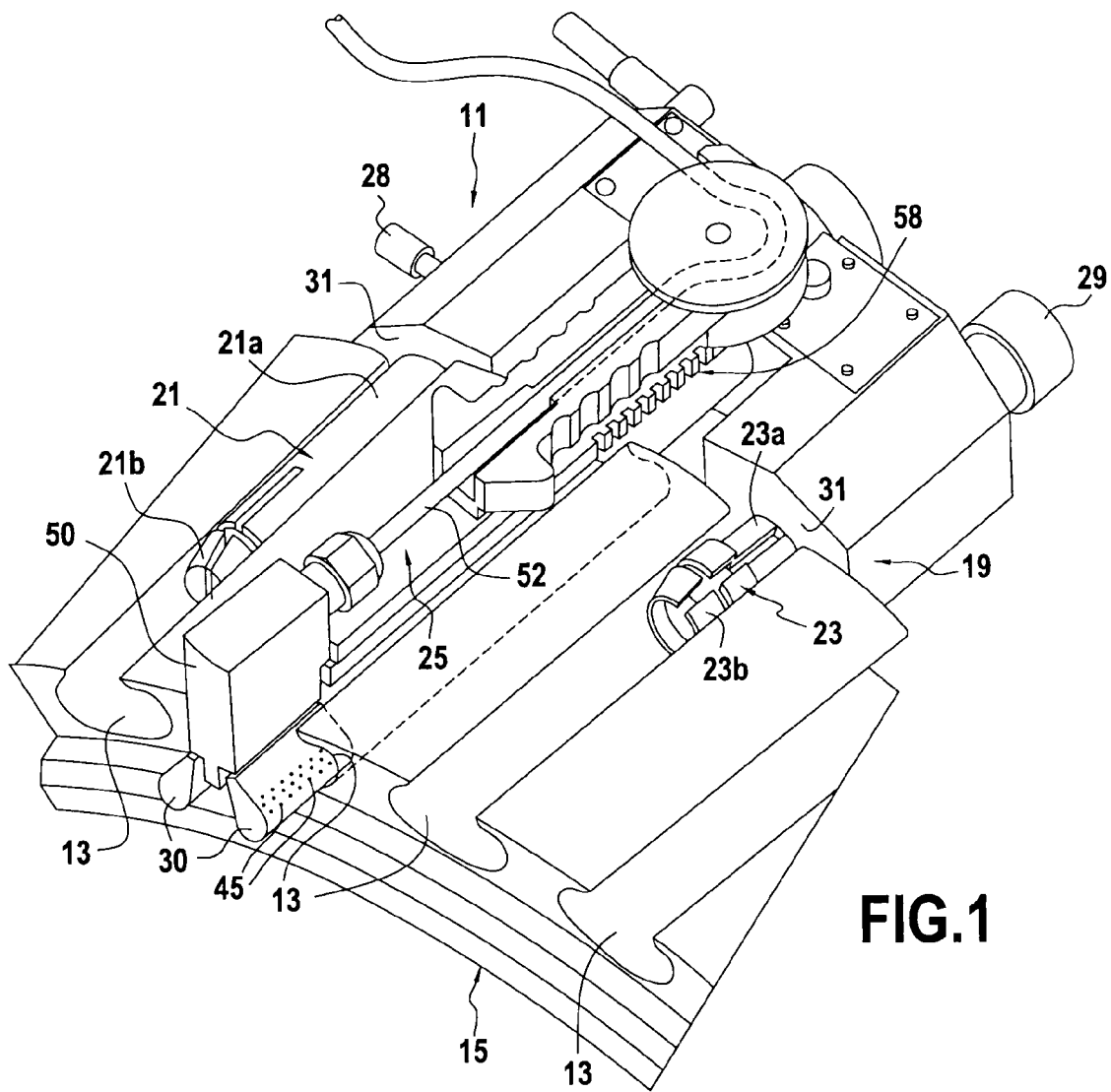
FIG. 1 is a general perspective view of the inspection device of the invention installed at the periphery of a rotor disk for inspecting one of its recesses by means of eddy currents.
Figure 2:
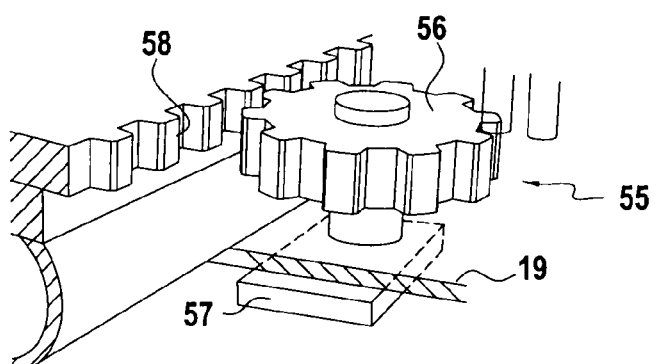
FIG. 2 is a detail view showing the indexing means.
Figure 3:
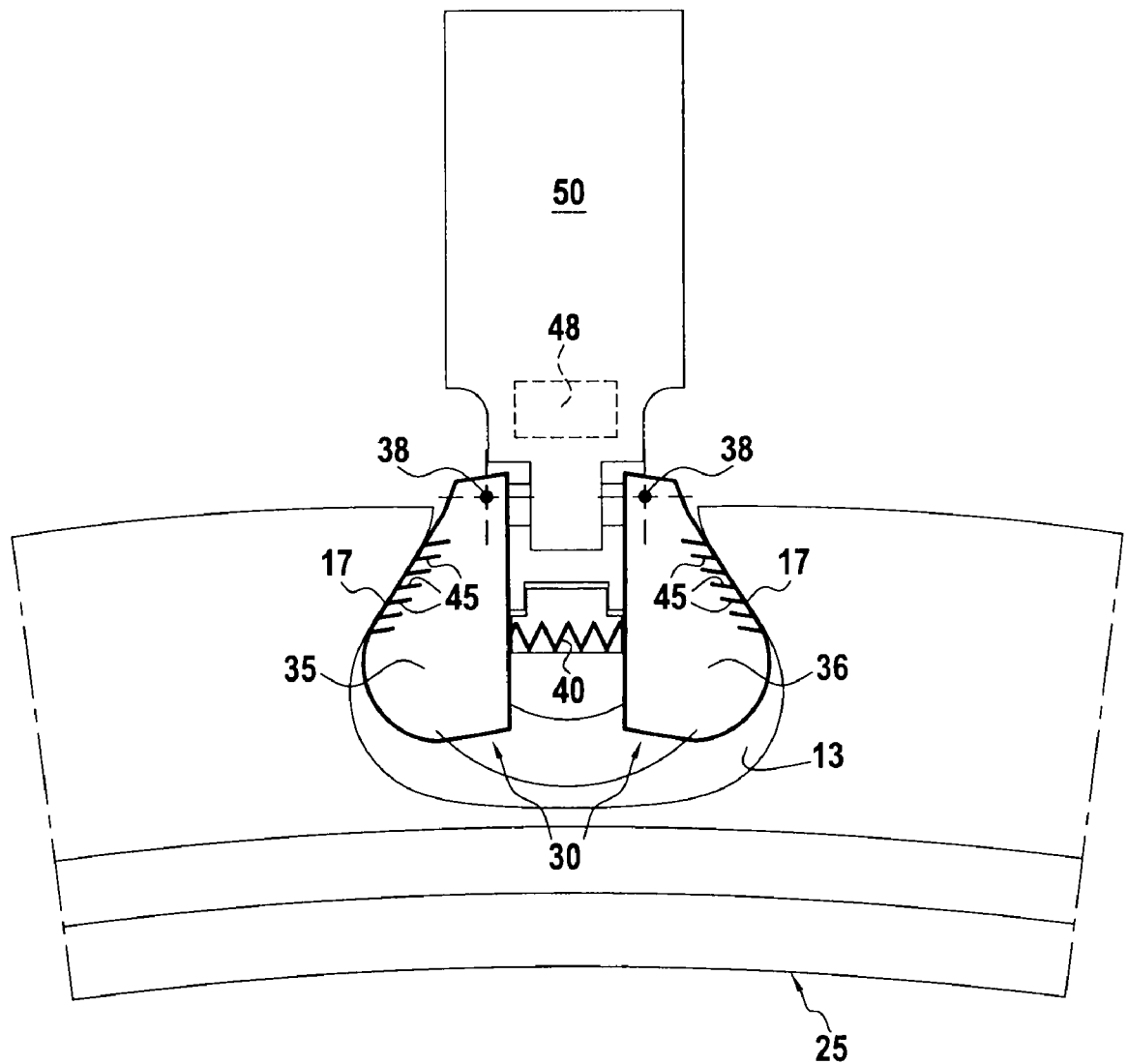
FIG. 3 is another detail view showing the structure of the probe.

With reference to the drawings, there is shown an eddy current inspection device 11 suitable for detecting defects at the surface (or close to the surface) in tangential recesses 13 defined at the periphery of a rotor disk 15. These recesses receive and maintain blade feet. Such a recess 13 includes in particular two so-called "pressure surfaces" 17 against which the root of a blade bears strongly under the effect of centrifugal force. It is very important to inspect the state of these pressure surfaces, particularly when performing verifications during routine maintenance. This serves to reveal the formation of fatigue cracks in the pressure surfaces.

The device comprises a support 19 having two positioning members 21 and 23 that are suitable for co-operating respectively with each of the recesses neighboring to the recess for inspection. These positioning members are formed by parallel rods 21a and 23a, each having an annular expandable element 21b or 23b. These rods are provided with expandable elements and they are spaced apart at a distance corresponding to the distance between recesses neighboring the recess for inspection, and more particularly in this example between the two nearest recesses situated on either side thereof. The support 19 is generally in the form of a bridge and carries sliding movement equipment 25 having a multi-element type eddy current probe 30 mounted thereon. The moving equipment slides along a slideway defined in the support. The assembly is arranged so that the probe 30 can engage in the tangential recess for inspection when the two rods 21a and 23a are engaged in the two neighboring recesses and are locked therein by using the expandable elements 21b and 23b. There can be seen a stationary rod 21a that is designed to be the first to be engaged in a neighboring recess, and a moving rod 23b that is slidable in the support 19 suitable for being inserted subsequently in the other neighboring recess.

The expandable element 21b of the stationary rod is controlled by a lateral lever 28, while the expandable element 23b of the moving rod is controlled by a knob 29 situated at the rear end thereof.

The support 19 has two abutment surfaces 31. The rods 21a and 23a project from respective ones of the surfaces.

Once the two rods have been locked in the two neighboring recesses, on either side of the recess for inspection, the support is positioned in such a manner that the abutment surfaces 31 bear against one side of the disk 15 and the moving equipment and the probe are exactly in register with one of the recess for inspection so that said probe can be engaged therein.

The probe 30 could be constituted by a single block of plastics material containing the sensors. Such a block would have a cross-section of outline matching at least a portion of the outline of the section of the recess 13. Nevertheless, in the example described, the probe 30 comprises two symmetrical blocks 35 and 36 that are hinged on parallel pivot axes 38, being biased resiliently outwards, i.e. away from each other, by means of a spring 40. This arrangement guarantees contact between the blocks and the corresponding zones of the recess for inspection, and more precisely in this example said pressure surfaces 17. This type of configuration means that the blocks need to be moved towards each other while inserting the probe into the recess.

Eddy current sensors 45 are placed on a plurality of lines within each block 35 and 36, so as to obtain overlap during movement of the probe along the tangential recess. The sensors can be distributed over substantially the entire length of the probe, including at its ends. In particular, it is advantageous for a plurality of sensors 45 to be disposed at the front of the probe 30 (relative to its direction of movement). Preferably, it is possible to place the largest possible number of sensors at the front of each block 35 so as to enable the end of the tangential recess to be scanned, even if it does not open out.

The wires of the sensors are connected to a multiplexed multi-channel generator-receiver 48 that enables all of the sensors to be caused to emit simultaneously and that serves to synchronize acquisitions on reception. The generator-receiver is used with the probe located in various positions along said recess for inspection. Such a generator-receiver 48 can be installed in the unit 50 (forming part of the moving equipment) to which the blocks are hinged. An electric cable 52 for transferring signals connects the generator-receiver to an imager device (not shown) including reconstruction software and image processor software enabling a readable acquisition to be constructed for playback in the so-called "C-SCAN" format.

In order to improve image playback, the device is also fitted with index means 55 for monitoring the position and/or the advance of the probe 30 in the recess for inspection. For example, a pinion 56 is mounted on the support 19. Its axle is connected to a pulse generator 57 or the like. The pinion meshes with a rectilinear rack 58 carried by the sliding moving equipment 25.

Thus, data acquisition is relatively independent of the operator, and in particular of the speed with which the operator moves the moving equipment carrying the probe. The moving equipment could be motor driven so as to scan at a predetermined, constant speed.

What is claimed is:

1. An inspection device for inspecting tangential recesses in a rotor disk by means of eddy currents, the device comprising:
   a probe of cross-section with an outline that matches the outline of the section of such a recess,
   wherein said probe includes
   a plurality of sensors arranged for acquiring a plurality of data series during a scan stroke in the longitudinal direction of the recess,
   a support with two positioning members, each of said positioning members includes a rod extending from the support which is inserted and cooperates respectively with two recesses neighboring the recess for inspection, and
   sliding moving equipment carrying said probe and arranged to guide said probe along said recess during inspection.

2. An inspection device according to claim 1, wherein the two positioning members include two expandable elements spaced apart by a distance corresponding to the distance between said neighboring recesses, said elements being arranged to be engaged and locked therein to position said support in such a manner that said probe can be engaged in said tangential recess for inspection.

3. A device according to claim 1, including indexing means for monitoring at least one of the position the progress of the probe in said recess for inspection.

4. A device according to claim 1, wherein said sensors are distributed in blocks of the probe, the blocks being hinge-mounted with outwardly-directed resilient bias so as to guarantee that said blocks make contact against the corresponding zones of said recess for inspection.

5. A device according to claim 1, including a multi-channel generator-receiver for activating all of the sensors substantially simultaneously at different positions along the probe in said recess for inspection.

6. A device according to claim 1, wherein the sensors are disposed at the leading end of the probe.

* * * * *